United States Patent
Ishizuka et al.

(10) Patent No.: US 9,833,764 B2
(45) Date of Patent: Dec. 5, 2017

(54) CHEMICAL REACTION APPARATUS

(71) Applicant: Microwave Chemical Co., Ltd., Osaka (JP)

(72) Inventors: Akinori Ishizuka, Osaka (JP); Keiji Kidani, Osaka (JP); Yukari Deguchi, Osaka (JP); Kunitaka Momota, Osaka (JP); Yasunori Tsukahara, Osaka (JP)

(73) Assignee: MICROWAVE CHEMICAL CO., LTD., Osaka-Shi, Osaka (JP)

( * ) Notice: Subject to any disclaimer, the term of this patent is extended or adjusted under 35 U.S.C. 154(b) by 0 days.

(21) Appl. No.: 14/888,758

(22) PCT Filed: Feb. 25, 2015

(86) PCT No.: PCT/JP2015/055336
§ 371 (c)(1),
(2) Date: Nov. 3, 2015

(87) PCT Pub. No.: WO2015/129723
PCT Pub. Date: Sep. 3, 2015

(65) Prior Publication Data
US 2016/0082409 A1    Mar. 24, 2016

(30) Foreign Application Priority Data

Feb. 27, 2014  (JP) ................................ 2014-036728

(51) Int. Cl.
*B01J 19/12*        (2006.01)
*C07C 67/03*        (2006.01)
(Continued)

(52) U.S. Cl.
CPC .......... *B01J 19/126* (2013.01); *B01J 8/0207* (2013.01); *B01J 8/0403* (2013.01); *B01J 19/245* (2013.01);
(Continued)

(58) Field of Classification Search
None
See application file for complete search history.

(56) References Cited

U.S. PATENT DOCUMENTS 5,393,320 A    2/1995 Gomez
5,732,476 A    3/1998 Pare
(Continued)

FOREIGN PATENT DOCUMENTS

CN    1729049 A    2/2006
CN    1946477 A    4/2007
(Continued)

OTHER PUBLICATIONS

Japanese Office Action dated May 2, 2014 issued in corresponding Japanese Patent Application No. 2014-036728.
(Continued)

*Primary Examiner* — Kishor Mayekar
(74) *Attorney, Agent, or Firm* — Troutman Sanders LLP

(57) ABSTRACT

In order to provide a chemical reaction apparatus that can suppress a situation where microwaves are concentrated on a partial portion in a reactor, and that can more uniformly irradiate a content with the microwaves, a chemical reaction apparatus includes: a horizontal flow-type reactor in which a liquid content horizontally flows with an unfilled space being provided thereabove; a microwave generator that generates microwaves; and a waveguide that transmits the microwaves generated by the microwave generator to the unfilled space in the reactor, wherein a top of the reactor is curved with respect to a flow direction of the content.

7 Claims, 18 Drawing Sheets

(51) Int. Cl.
*C07C 67/08* (2006.01)
*B01J 19/24* (2006.01)
*B01J 8/02* (2006.01)
*B01J 8/04* (2006.01)
*H05B 6/64* (2006.01)
*H05B 6/70* (2006.01)
*H05B 6/80* (2006.01)

(52) U.S. Cl.
CPC .............. *C07C 67/03* (2013.01); *C07C 67/08* (2013.01); *H05B 6/645* (2013.01); *H05B 6/707* (2013.01); *H05B 6/806* (2013.01); *B01J 2219/00063* (2013.01); *B01J 2219/0871* (2013.01); *B01J 2219/0877* (2013.01); *B01J 2219/129* (2013.01); *B01J 2219/1224* (2013.01); *B01J 2219/1245* (2013.01); *B01J 2219/1269* (2013.01); *B01J 2219/1281* (2013.01); *B01J 2219/1296* (2013.01); *B01J 2219/182* (2013.01); *B01J 2219/1941* (2013.01); *H05B 2206/044* (2013.01)

(56) References Cited

U.S. PATENT DOCUMENTS

| | | | |
|---|---|---|---|
| 2002/0023922 A1 | 2/2002 | Lee et al. | |
| 2004/0056026 A1* | 3/2004 | Jakes | C03B 5/023 219/701 |
| 2007/0295717 A1* | 12/2007 | Horikawa | B01J 19/126 219/710 |
| 2010/0172202 A1* | 7/2010 | Borgstadt | B01F 13/1013 366/15 |
| 2013/0102047 A1* | 4/2013 | Ishizuka | C12N 1/12 435/173.7 |
| 2014/0121395 A1 | 5/2014 | Ishizuka et al. | |
| 2014/0363348 A1 | 12/2014 | Ishizuka et al. | |
| 2015/0004069 A1 | 1/2015 | Ishizuka | |

FOREIGN PATENT DOCUMENTS

| | | |
|---|---|---|
| EP | 2385146 A1 | 11/2011 |
| EP | 2845645 A1 | 3/2015 |
| JP | H02-066497 A | 3/1990 |
| JP | H10-050470 A | 2/1998 |
| JP | 2002-061847 A | 2/2002 |
| JP | 2007-307440 A | 11/2007 |
| JP | 2011-235262 A | 11/2011 |
| JP | 5213199 B1 | 6/2013 |
| WO | 2004/056471 A1 | 7/2004 |
| WO | 2010/087464 A1 | 8/2010 |
| WO | WO 2012/002483 * | 5/2012 |
| WO | 2013001629 A1 | 1/2013 |
| WO | 2013/069778 A1 | 5/2013 |
| WO | 2013/069779 A1 | 5/2013 |

OTHER PUBLICATIONS

Decision of Rejection dated Aug. 6, 2014 issued in corresponding Japanese Patent Application No. 2014-036728.
International Search Report dated May 26, 2015 issued in corresponding PCT Application No. PCT/JP2015/055336.
Chinese Office Action dated Jun. 30, 2016 issued in corresponding Chinese Patent Application No. 201580000537.0.
Chinese Second Office Action dated Nov. 15, 2016 issued in corresponding Chinese Patent Application No. 201580000537.0.
Extended European Search Report dated Dec. 19, 2016 issued in corresponding European Application No. 15754690.4.

* cited by examiner

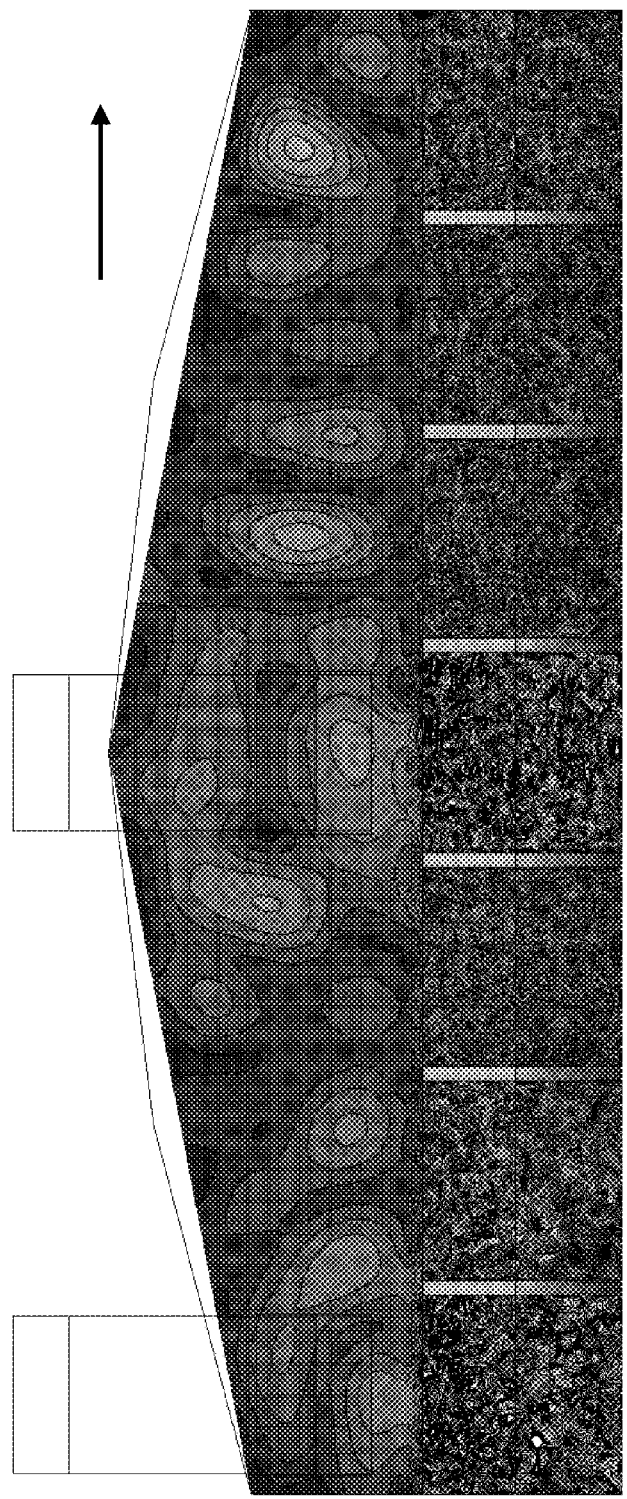

CHEMICAL REACTION APPARATUS

CROSS-REFERENCE TO RELATED APPLICATIONS

This is a U.S. national phase application under 35 U.S.C. §371 of International Patent Application No. PCT/JP2015/055336, filed Feb. 25, 2015, and claims benefit of priority to Japanese Patent Application No. 2014-036728, filed Feb. 27, 2014. The International Application was published Sep. 3, 2015 as International Publication No. WO/2015/129723 under PCT Article 21(2). The entire contents of these applications are hereby incorporated herein by reference.

TECHNICAL FIELD

The present invention relates to a chemical reaction apparatus for irradiating a liquid content in a reactor with microwaves.

BACKGROUND ART

Conventionally, chemical reaction apparatuses for irradiating a content with microwaves (e.g., electromagnetic waves), are known, thereby performing heating or the like of the content. See, for example, Japanese Patent Application No. JP 2011-235262A.

SUMMARY

Conventional heating using a heater is external heating that gradually applies heat from the surface of a material toward the internal portion by thermal conduction, radiation, convection, or the like. Meanwhile, heating using microwaves is characterized in that it is internal heating that causes a material itself to generate heat. However, during irradiation with microwaves, the microwaves may be concentrated on a partial portion in a reactor. If microwaves are concentrated in this manner, a problem occurs that the partial portion in the reactor is abnormally heated. Such microwave concentration further causes a problem that some portions are not irradiated with microwaves so that the content is not properly heated.

The present invention was arrived at in order to solve the above-described problems, and it is an object thereof to provide a chemical reaction apparatus that can irradiate a content in a reactor with microwaves as uniformly as possible.

In order to achieve the above-described object, the present invention is directed to a chemical reaction apparatus, including: a reactor having a shape horizontally extending in one direction, in which a liquid content is placed with an unfilled space being provided thereabove; a microwave generator that generates microwaves; and a waveguide that transmits the microwaves generated by the microwave generator to the unfilled space in the reactor; wherein a top of the reactor is curved with respect to a longitudinal direction of the reactor.

With this configuration, the inside of the reactor can be more uniformly irradiated with microwaves.

In the chemical reaction apparatus according to the present invention, the top of the reactor may be arched with respect to a direction orthogonal to the longitudinal direction of the reactor.

With this configuration, a situation where microwaves are concentrated on part of the unfilled space can be avoided, and the inside of the reactor can be more uniformly irradiated with microwaves.

In the chemical reaction apparatus according to the present invention, an angle formed by microwaves incident on the unfilled space and a liquid surface of the content may be 30 to 75 degrees.

With this configuration, the content can be more uniformly irradiated with microwaves.

In the chemical reaction apparatus according to the present invention, the microwaves may be irradiated on a middle position in the direction orthogonal to the longitudinal direction of the reactor.

The present invention is further directed to a chemical reaction apparatus, including: a reactor having a shape horizontally extending in one direction, in which a liquid content is placed with an unfilled space being provided thereabove; a microwave generator that generates microwaves; and a waveguide that transmits the microwaves generated by the microwave generator to the unfilled space in the reactor; wherein an angle formed by microwaves incident on the unfilled space and a liquid surface of the content is 30 to 75 degrees.

With this configuration, the content can be more uniformly irradiated with microwaves.

In the chemical reaction apparatus according to the present invention, the angle formed by the microwaves incident on the unfilled space and the liquid surface of the content may be 45 degrees.

In the chemical reaction apparatus according to the present invention, the reactor may be a horizontal flow-type reactor in which the content flows in the longitudinal direction of the reactor, or may be a batch-type reactor.

The chemical reaction apparatus according to the present invention can suppress a situation where microwaves are concentrated on a partial portion in a reactor, and can more uniformly irradiate a content with the microwaves.

BRIEF DESCRIPTION OF THE DRAWINGS

FIG. 7A is a diagram showing a simulation result (curved shape) in this example.

DETAILED DESCRIPTION

Figure 1:
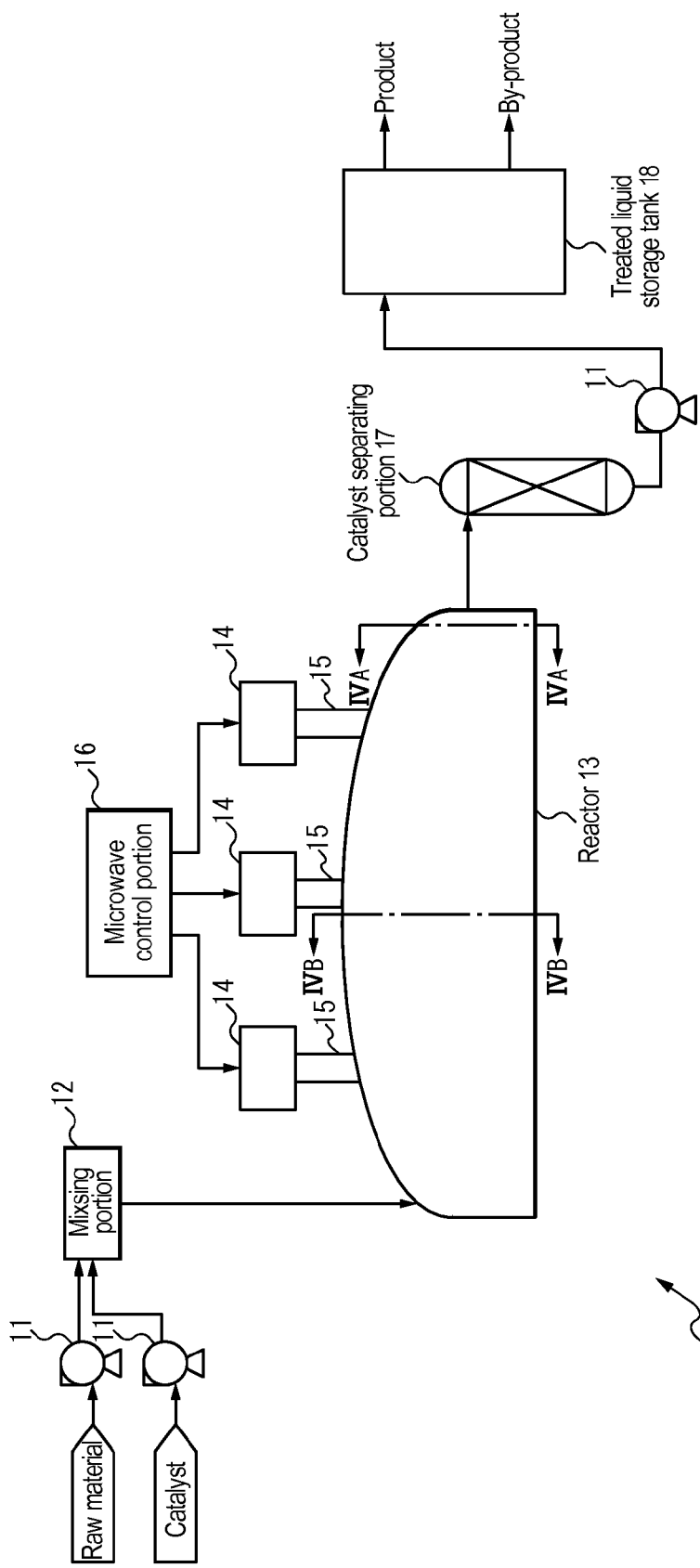
FIG. 1 is a diagram showing the configuration of a chemical reaction apparatus according to Example 1 of the present invention.

Hereinafter, examples of a chemical reaction apparatus according to the present invention will be described. Note that constituent elements denoted by the same reference numerals are the same as or similar to each other in the following examples, and, thus, a description thereof may not be repeated.

Example 1

Below, a chemical reaction apparatus according to Example 1 of the present invention will be described with reference to the drawings. The chemical reaction apparatus according to this example is such that the top of a reactor is curved with respect to a longitudinal direction of the reactor and is arched with respect to a direction orthogonal to the longitudinal direction.

FIG. 1 is a diagram showing the configuration of a chemical reaction apparatus 1 according to this example. The chemical reaction apparatus 1 according to this example includes a mixing portion 12, a reactor 13, microwave generators 14, waveguides 15, a microwave control portion 16, a catalyst separating portion 17, and a treated liquid storage tank 18.

The mixing portion 12 mixes a raw material and a solid catalyst. The mixing portion 12 may mix the raw material and the like with a reactant. The raw material may contain multiple materials. For example, in the case of performing esterification in the reactor 13, fat and oils and alcohol may be used as the raw material. The raw material and the solid catalyst may be supplied to the mixing portion 12 by pumps 11 as shown in FIG. 1, or may be supplied to the mixing portion 12 using other methods. The mixing portion 12 may mix two or more materials, for example, by rotating a blade-like member, a wing-like member, or a screw-like member. Note that, although this example describes the case in which the catalyst that is to be mixed with the raw material is a solid catalyst (i.e., heterogeneous catalyst), the catalyst may be a liquid catalyst (i.e., homogeneous catalyst). The solid catalyst may or may not form a fluidized bed inside the reactor 13. There is no limitation on the shape of the solid catalyst. Examples of the shape of the solid catalyst include various grains, a cylinder (that may or may not be hollow, for example), a sphere, a pellet, a ring, a shell, and other shapes. The solid catalyst may or may not be, for example, microwave-absorbing or microwave-sensitive. If the solid catalyst is microwave-absorbing or microwave-sensitive, when microwave irradiation is performed inside the reactor 13 (described later), the solid catalyst is heated by the microwaves, and the chemical reaction near the solid catalyst is facilitated. Note that the microwave absorptivity and the microwave sensitivity depend on the frequency of microwaves used for irradiation, the temperature inside the reactor 13, and the like. That is to say, materials that have a high dielectric loss factor, at the frequency of microwaves used and the temperature inside the reactor 13 in which the raw material is to undergo a reaction, provide a high microwave absorptivity. Accordingly, for example, a solid catalyst containing such a highly microwave-absorbing material may be used. For example, if microwaves at 2.45 GHz are irradiated, examples of the microwave-absorbing material include carbon (e.g., graphite, carbon nanotube, activated carbon, etc.) except for fullerene, iron, nickel, cobalt, ferrite, and the like. Accordingly, the solid catalyst may contain such a microwave-absorbing material. Specifically, the solid catalyst may be a composite in which such a microwave-absorbing or microwave-sensitive material and a metal or metal oxide are combined, a composite in which such a microwave-absorbing or microwave-sensitive material and a catalyst such as alkali catalyst or acid catalyst are combined, or a composite in which a microwave-absorbing or microwave-sensitive material, a catalyst such as alkali catalyst or acid catalyst, and a metal or metal oxide are combined. The composite may be formed, for example, through physical adsorption, chemical bonding, alloying, or other methods. Furthermore, in the mixing portion 12, preliminary heating may or may not be performed for preparation for the reaction in the reactor 13. In the case of performing the preliminary heating, the temperature in the preliminary heating in the mixing portion 12 is preferably controlled such that the raw material and the like at the time of entering the reactor 13 are at a desired temperature or in a desired temperature range. Note that, in the case of not performing the preliminary heating in the mixing portion 12, heating corresponding to the preliminary heating may be performed in the reactor 13. The raw material and the solid catalyst mixed by the mixing portion 12 are loaded into the reactor 13.

The reactor 13 is a reaction unit having a shape horizontally extending in one direction, in which a liquid content is placed with an unfilled space being provided thereabove. That is to say, the reactor 13 has a shape extending in one direction, and is installed such that the longitudinal direction thereof matches the horizontal direction. The reactor 13 may be of a flow-type, or may be of a batch-type. In the former case, the reactor 13 is a horizontal flow-type reaction unit in which a liquid content horizontally flows with an unfilled space being provided thereabove. The direction in which the content flows is the longitudinal direction of the reactor 13. This example mainly describes a case in which the reactor 13 is of a flow-type. In the reactor 13 shown in FIG. 1, the left-right direction in the drawing is the longitudinal direction of the reactor 13, and the content flows from the left to the right in the drawing. Accordingly, the content is loaded on the upstream side in the reactor 13, that is, on the left side in the drawing. Examples of the content of the reactor 13 include a mixture of the raw material and the catalyst. The raw material and the catalyst mixed by the mixing portion 12 flow inside the reactor 13. Note that, since the chemical reaction in the reactor 13 produces a product material from the raw material, the content of the reactor 13 may be considered to contain the product material. That is to say, the content may be referred to as the raw material and/or the product material. Since an unfilled space is present above the content, the content is typically a material other than gas. The content can flow inside the reactor 13 and has a flat liquid surface, and, thus, the content is a material other than solid (e.g., powders or grains, etc.). Accordingly, the content is liquid. The liquid content may be, for example, a material having a high flowability such as water, oil, aqueous solution, or colloidal solution, or may be a material having a low flowability such as slurry or suspension. It is preferable that the liquid surface of the content inside the reactor 13 is kept horizontal, and, thus, even in the case where the flowability of the liquid content is low, it preferably allows the liquid surface to be horizontal after a while without the application of vibration from the outside. That is to say, the liquid content preferably has a flowability that allows the shape of the surface to be changed without vibration from the outside. Note that the liquid surface being horizontal may refer to the state of being completely flat, or may refer to the state of being flat on the whole although there are slightly rough portions. The reason for this is that, if the content does not have a high flowability, the liquid surface may not be completely flat. The inner wall of the reactor 13 is preferably made of a microwave-reflecting material. Examples of the microwave-reflecting material include metal. The internal configuration of the reactor 13 will be described later. The state in which the longitudinal direction of the reactor 13 matches the horizontal direction may refer to a state in which the longitudinal direction of the reactor 13 strictly matches the horizontal direction, and may include a state in which the longitudinal direction of the reactor 13 is inclined with respect to the horizontal direction within a range that allows the content to flow from the upstream side to the downstream side or within a range of errors such as measurement errors or design errors.

The microwave generators 14 generate microwaves. The chemical reaction apparatus 1 according to this example may include one microwave generator 14, or may include two or more microwave generators 14. There is no limitation on the frequency of the microwaves, and examples thereof include 2.45 GHz, 5.8 GHz, 24 GHz, 915 MHz, and other frequencies ranging from 300 MHz to 300 GHz. If the chemical reaction apparatus 1 includes two or more microwave generators 14, the frequency of the microwaves generated by the microwave generators 14 may be the same, or may be different from each other. In the latter case, for example, microwave irradiation at a frequency A may be performed on the upstream side in the flow direction in the reactor 13 and microwave irradiation at a frequency B may be performed on the downstream side, or microwave irradiation at frequencies A and B may be performed at the same position in the flow direction in the reactor 13. Note that it is assumed that the frequency A and the frequency B are different from each other.

The waveguides 15 transmit the microwaves generated by the microwave generators 14 to the unfilled space in the reactor 13. The number of waveguides 15 provided may be the same as the number of microwave generators 14 as shown in FIG. 1. Furthermore, the waveguide 15 may be branched and transmit the microwaves to two or more positions in the unfilled space. Note that the specification of the waveguides 15 is preferably in accordance with the frequency of the microwaves generated by the microwave generators 14.

The microwave control portion 16 controls the output (power) of microwaves used for irradiation in the reactor 13, according to the temperature measured by temperature measuring portions 25 (described later). The control by the microwave control portion 16 makes it possible to keep inside the reactor 13 at a desired temperature or in a desired temperature range.

The catalyst separating portion 17 separates the catalyst from the product material after the reaction in the reactor 13. If the catalyst that has been mixed with the raw material is a solid catalyst, for example, filtering may be used to separate the solid catalyst, or one of the solid catalyst and the product material may be precipitated to separate the solid catalyst. Furthermore, if the solid catalyst contains a magnetic substance, a magnet for attracting the solid catalyst may be used to separate the solid catalyst. Note that the separated solid catalyst may be used again as appropriate. Furthermore, if a liquid catalyst is used, distillation, extraction, or neutralization may be performed in the catalyst separating portion 17 to separate the catalyst.

The product material from which the catalyst has been separated by the catalyst separating portion 17 is loaded into the treated liquid storage tank 18. Then, this product material is separated as appropriate into a final product, a by-product, and the like. For example, if the raw material is free fatty acid and esterification is performed in the reactor 13, a product that is biodiesel fuel and a by-product that is water are obtained. In this case, an acid catalyst is used. Furthermore, for example, if the raw material is triglyceride and transesterification is performed in the reactor 13, a product that is biodiesel fuel and a by-product that is glycerin are obtained. In this case, an alkali catalyst is used.

Note that an unshown cooler that cools down the material after the reaction in the reactor 13 may or may not be provided on the path after the reactor 13. In the former case, for example, the cooler may use water to cool down the material after the reaction in the reactor 13.

Figure 2:
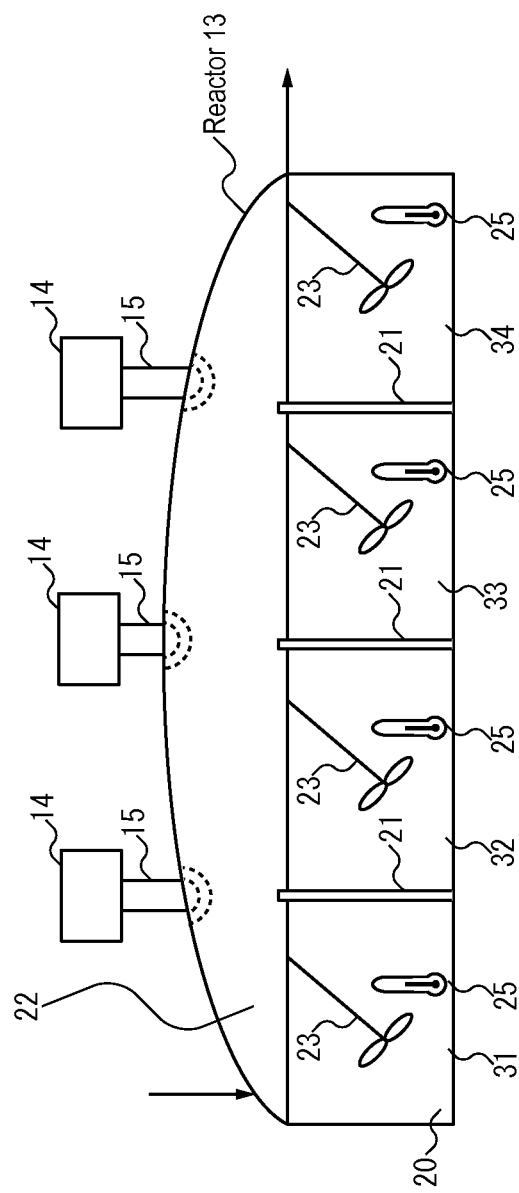
FIG. 2 is a diagram showing an example of the internal configuration of a reactor in this example.

FIG. 2 is a diagram showing an example of the internal configuration of the reactor 13 according to this example. It is preferable that an unfilled space 22 is present throughout the longitudinal direction of the reactor 13 (e.g., the left-right direction in FIG. 2) as shown in FIG. 2, but there is no limitation to this. In FIG. 2, the inside of the reactor 13 is partitioned by partition plates 21 into multiple chambers 31, 32, 33, and 34. The multiple chambers 31, 32, 33, and 34 are chambers that are continuously arranged in series. As described above, the unfilled space 22 is present in the upper portion inside the reactor 13. The unfilled space 22 is irradiated with the microwaves generated by the microwave generators 14 and transmitted via the waveguides 15. Note that FIG. 2 shows the case in which a single unfilled space is present inside the reactor 13, that is, the case in which an unfilled space is shared by all the chambers 31 to 34, but there is no limitation to this. That is to say, an unfilled space may be shared by at least two or more chambers that are part of all chambers, or may be shared by none of the chambers. In this case, there are unfilled spaces that have been separated from each other by the partition plates 21. The waveguides 15 may or may not be provided at the positions around the middle in the chambers 32, 33, and 34. In the former case, for example, the microwaves that have been transmitted by one waveguide 15 to the unfilled space 22 are mainly irradiated on the chamber present therebelow. Since microwaves are transmitted through an unfilled space, for example, the microwaves that have been transmitted by the waveguide 15 at the position of the chamber 32 are irradiated via the unfilled space also on the content in the chamber 31 and the chamber 33. Note that the waveguides 15 may be provided at the positions of the partition plates 21, that is, at the positions above the partition plates 21. Accordingly, the microwaves that have been transmitted by one waveguide 15 to the unfilled space 22 are mainly irradiated on two chambers that have been partitioned from each other by the partition plate 21 at the position corresponding to that waveguide 15. If the unfilled space is shared by multiple chambers, the microwaves that have been transmitted to the shared unfilled space are irradiated on a content 20 in the multiple chambers sharing the unfilled space. The partition plates 21 may transmit microwaves, may absorb microwaves, or may reflect microwaves. Examples of the microwave-transmitting material include Teflon (registered trademark), quartz glass, ceramic, silicon nitride-alumina, and the like. Accordingly, the partition plates 21 that transmit microwaves may be made of such a microwave-transmitting material. Furthermore, examples of the microwave-absorbing material include carbon except for fullerene, and the like. Accordingly, the partition plates 21 that absorb microwaves may be made of such a microwave-absorbing material. Furthermore, examples of the microwave-reflecting material include metal. Accordingly, the partition plates 21 that do not transmit microwaves may be made of such a microwave-reflecting material. Furthermore, the partition plates 21 may be made of a combination of two or more materials freely selected from the microwave-transmitting material, the microwave-absorbing material, and the microwave-reflecting material.

Furthermore, as shown in FIG. 2, the chemical reaction apparatus 1 may include one or more agitation units 23 that rotationally agitate the content 20 inside the reactor 13. FIG. 2 shows the case in which the chambers 31 to 34 respectively have the agitation units 23, but there is no limitation to this. One or more chambers may have no agitation unit 23. Furthermore, FIG. 2 shows the case in which each of the agitation units 23 is in the shape of a blade, but this merely schematically shows the agitation units 23. The agitation may be performed, for example, by rotating a blade-like, wing-like, or rod-like rotatable member. The rotatable member may be made of a microwave-transmitting material, a microwave-absorbing material, a microwave-reflecting material, or a combination of two or more materials freely selected from the microwave-transmitting material, the microwave-absorbing material, and the microwave-reflecting material. The rotation may be performed, for example, by rotating a rotatable member attached to a shaft in accordance with the rotation of the shaft, or by rotating the rotatable member using a magnetic force as in the case of a magnetic stirrer. In the former case, the shaft may be provided independently for each chamber, or may be shared by multiple chambers. In the latter case, the rotatable member (magnetic stirrer) in the shape of a rod, a blade, a wing, or the like is rotated by a magnet. The agitation of the content by the agitation units 23 may be used to cause the content to flow from the upstream side to the downstream side, or in the opposite direction, but there is no limitation to this. Note that rotational agitation is already known, and, thus, a detailed description thereof has been omitted.

Hereinafter, reasons why the content of the reactor 13 is rotationally agitated by the agitation units 23 will be briefly described. A first reason why the content is agitated by the agitation units 23 is to uniformly heat the content with microwaves. Although depending on the type of content and the temperature of the content, the depth to which microwaves penetrate is fixed, and, thus, the agitation is performed in order to uniformly irradiate and uniformly heat the entire content with microwaves. Furthermore, the content can be more efficiently irradiated with microwaves as the surface area of the content at the unfilled space 22 increases. Accordingly, a second reason why the content is agitated is to increase the area subjected to microwave irradiation. Thus, the content is agitated by the agitation units 23 preferably at an intensity that allows the surface of the content at the unfilled space 22 to be disordered, but there is no limitation to this. If the agitation is performed for the first reason, it may be sufficient that the entire content is eventually heated. Furthermore, since the raw material and the like are agitated using the agitation units 23 in this manner, even in the case where a raw material contains two or more materials having different densities, these materials can be mixed and reacted with each other as appropriate. For example, when causing materials having different densities, such as alcohol and waste oil, to react with each other in a vertical flow-type reactor, these materials are easily separated from each other. However, as in this example, if the reactor 13 is of a horizontal flow-type and is provided with the agitation units 23, these materials can be mixed and reacted with each other as appropriate.

Furthermore, as shown in FIG. 2, the reactor 13 also may have the temperature measuring portions 25. That is to say, the chemical reaction apparatus 1 according to this example may have the temperature measuring portions 25 that measure the temperature inside the reactor 13. The temperature inside the reactor 13 is preferably the temperature of the content of the reactor 13. FIG. 2 shows the case in which the chambers 31 to 34 respectively have the temperature measuring portions 25, but there is no limitation to this. One or more chambers may not have the temperature measuring portion 25. Furthermore, FIG. 2 merely schematically shows the temperature measuring portions 25. The temperature measuring portions 25 may measure the temperature, for example, using a thermocouple, an infrared sensor, an optical fiber, or other methods. The temperature measured by the temperature measuring portions 25 is passed to the microwave control portion 16, and is used to control the output of microwaves from the microwave generators 14. Strictly speaking, the temperature passed to the microwave control portion 16 is data indicating the temperature. As described above, this control may be control for keeping the temperature in the chambers 31 to 34 at a desired temperature or in a desired temperature range. For example, if microwaves are irradiated on the position of each partition plate 21 as shown in FIG. 2, the output of microwaves irradiated on that position may be controlled, for example, using one of the temperatures in two chambers that have been partitioned from each other by the partition plate 21 at the position subjected to the microwave irradiation, or both of the temperatures. In the former case, for example, the control may be performed using a lower temperature, using a higher temperature, or using a temperature in a chamber specified in advance. In the latter case, for example, the control may be performed using an average of these temperatures, or using a weighted average according to the capacities of both chambers (i.e., average in consideration of weights according to the capacities of the chambers).

Hereinafter, the shape of the top of the reactor 13 will be described. As shown in FIGS. 1 and 2, the top of the reactor 13 is curved with respect to the longitudinal direction of the reactor 13 (e.g., the left-right direction in FIGS. 1 and 2). The curved shape is a curved shape projecting upward. That is to say, the ceiling side of the reactor 13 is shaped such that the height in the upper-lower direction (vertical direction) of the unfilled space 22 is highest around the middle in the longitudinal direction and is gradually lowered toward both ends of the reactor 13. Note that both ends of the reactor 13 are an inlet side and an outlet side of the reactor 13. The curved shape may be, for example, a semi-elliptic shape, an arc shape, or the like. Strictly speaking, the shape of the top of the reactor 13 refers to the shape of the top of the inside (i.e., the unfilled space 22) of the reactor 13. The same is applied to the description below. The flow direction in the reactor 13 may be considered to be the longitudinal direction of the horizontal flow-type reactor 13.

Figure 3:
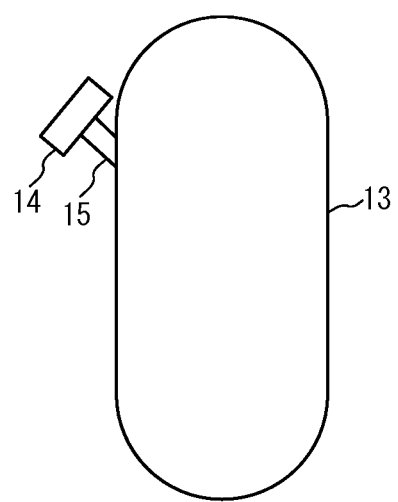
FIG. 3 is a diagram showing the shape of the reactor in this example.
Figure 4A:
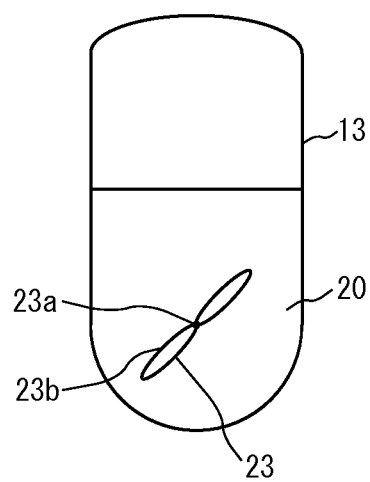
FIG. 4A is a vertical cross-sectional view of the reactor in this example.
Figure 4B:
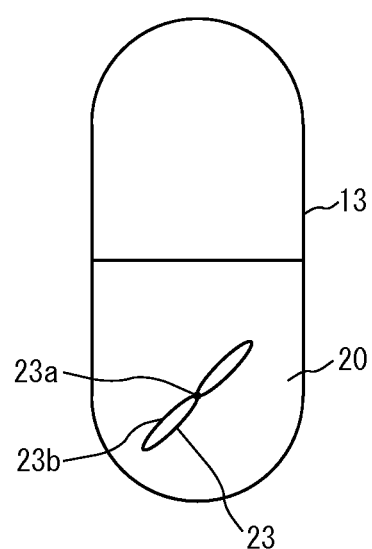
FIG. 4B is a vertical cross-sectional view of the reactor in this example.

FIG. 3 is a diagram showing the external shape of the reactor 13 viewed in the longitudinal direction thereof. FIG. 4A is a cross-sectional view taken along the line IVA-IVA in FIG. 1. FIG. 4B is a cross-sectional view taken along the line IVB-IVB in FIG. 1. Although each of FIGS. 4A and 4B shows a shaft 23*a* and a rotatable member 23*b* of one of the agitation units 23, some cross-sections may have no rotatable member 23*b* depending on the positions of the cross-sections. In these cross-sectional views, the top of the reactor 13 is arched. That is to say, the top of the reactor 13 is arched with respect to a direction orthogonal to the longitudinal direction of the reactor 13. The direction orthogonal to the longitudinal direction may be considered to be a horizontal direction, among the directions orthogonal to the longitudinal direction. The arched shape is an arched shape projecting upward. That is to say, the ceiling side of the reactor 13 is shaped such that the height in the upper-lower direction (vertical direction) of the unfilled space 22 is highest around the middle in the direction orthogonal to the longitudinal direction of the reactor 13 and is gradually lowered toward the side faces of the reactor 13. The arched shape may be, for example, a semi-circular shape, a semi-elliptic shape, or other arched shapes. Since the top of the reactor 13 is curved with respect to the longitudinal direction, the height of the unfilled space in FIG. 4A is lower than that in FIG. 4B. The cross-sectional shape on the lower side of the reactor 13 may be a semi-circular shape projecting downward as shown in FIGS. 4A and 4B, or may be other shapes. In the former case, even when the rotatable member 23*b* rotates about the shaft 23*a*, the rotatable member 23*b* can be prevented from interfering with the internal face of the reactor 13, and, furthermore, a gap between the rotatable member 23*b* and the reactor 13 can be reduced, so that the amount of content left unagitated and remaining at part of the reactor 13 can be reduced. Note that, as shown in FIGS. 4A and 4B, a region in which the width in the horizontal direction does not change may exist between the arched portion on the top and the semi-circular portion on the lower side in the vertical cross-section of the reactor 13. In this case, if the liquid surface of the content 20 is within this region, the area of the liquid surface may not change even when the height of the liquid surface changes.

Figure 4C:
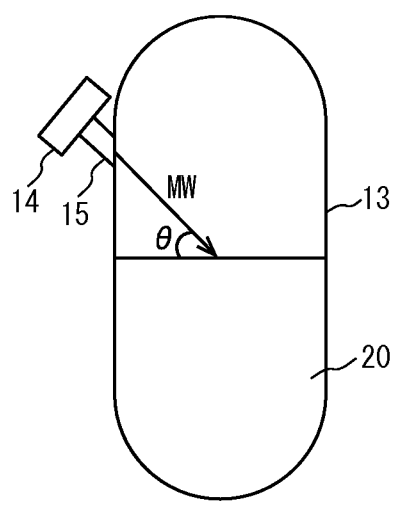
FIG. 4C is a vertical cross-sectional view of the reactor in this example.

FIG. 4C is a view illustrating an angle formed by microwaves incident on the unfilled space 22 and the liquid surface of the content 20. In FIG. 4C, the agitation units 23 are not shown. An angle θ formed by the microwaves and the liquid surface of the content 20 is preferably 30 to 75 degrees. If the angle is within this range, the content 20 can be more uniformly irradiated with microwaves as described later. The angle θ formed by the microwaves and the liquid surface of the content 20 is more preferably 45 degrees. Note that "45 degrees" may include angles different from 45 degrees within a range of errors such as measurement errors or design errors. The microwaves may be irradiated on the middle position of the liquid surface in the direction orthogonal to the flow direction of the content 20 (e.g., left-right direction in FIG. 4C). That is to say, the microwaves may be irradiated on the middle in the left-right direction on the liquid surface of the content 20 as shown in FIG. 4C. Accordingly, the microwaves that were reflected by the liquid surface are reflected by the ceiling side of the reactor 13 and are easily irradiated on the content 20 again. Note that the middle may include positions different from the middle within a range of errors such as measurement errors or design errors. The microwaves being irradiated on the middle position may be considered to be a situation in which, in a case where the waveguide 15 that transmits the microwaves is extended in the longitudinal direction, the extended waveguide intersects the liquid surface of the content at the middle position.

If the angle θ formed by the microwaves incident on the unfilled space and the liquid surface of the content 20 is 45° as shown in FIG. 4C, typically, openings of the waveguides 15 are seen in the unfilled space 22 in FIG. 2, but FIGS. 1 and 2 show the waveguides 15 at θ=90° for the sake of convenience of this description.

Next, the partition plates 21 will be described. The content 20 such as a raw material loaded into the reactor 13 flows through the chambers 31 to 34 and is finally discharged from the downstream side (e.g., the right end of the reactor 13 in FIG. 2). Note that a flow path that allows the content to flow is formed at the partition plates 21. The flow path allows the content to flow mainly from the upstream side (e.g., the left side in FIG. 2) to the downstream side (e.g., the right side in FIG. 2) in the reactor 13, but may allow part of the content to flow from the downstream side to the upstream side. The flow path at the partition plates 21 may be, for example, a flow path that allows the content to flow over the partition plates 21, or may be a flow path that allows the content to flow through a void of the partition plates 21. The partition plates 21 may be, for example, as described in JP 2013-103160A. Furthermore, if there are multiple partition plates 21 inside the reactor 13, the partition plates 21 may have the same shape, or may have different shapes.

Note that the height of the liquid surface inside the reactor 13 is on the whole determined by the position of the outlet of the reactor 13. Typically, the height of the liquid surface is higher than the position of the outlet, and, thus, the lower limit of the liquid surface can be determined by the position of the outlet. Furthermore, the height of the liquid surface in each chamber is determined by the height of the flow path between that chamber and a next chamber adjacent thereto. In this case, typically, the height of the liquid surface in each chamber is approximately the same as the position of the flow path through which the content flows out from that chamber, and, thus, the height of the liquid surface can be controlled by the position of that flow path. Typically, the height of the outlet from the reactor 13 is approximately the same as height of the flow path through which the content flows out from each chamber to the next chamber.

Furthermore, the wall face of the reactor 13 may be covered by a heat insulating material. In that case, heat inside the reactor 13 can be prevented from being dissipated to the outside.

Next, an operation of the chemical reaction apparatus 1 according to this example will be briefly described. The raw material and the catalyst are supplied by the pumps 11 to the mixing portion 12, are mixed in the mixing portion 12, and are loaded into the reactor 13. The speed of the raw material and the like supplied to the reactor 13 may be determined in advance.

The raw material and the like supplied to the reactor 13 flow from the upstream side to the downstream side while being agitated by the agitation units 23. At that time, the microwaves generated by the microwave generators 14 are transmitted via the waveguides 15 to the unfilled space 22 in the reactor 13, and are irradiated on the raw material and the like. As a result, the raw material and the like are heated, and the reaction of the raw material and the like is facilitated. Note that the temperatures in the chambers 31 to 34 are measured by the temperature measuring portions 25, and are passed to the microwave control portion 16 via a route that is not shown. Then, the microwave control portion 16 controls the output of the microwave generators 14 such that the temperatures in the chambers 31 to 34 are at a desired temperature or in a desired temperature range.

The product material discharged from the reactor 13 is loaded into the catalyst separating portion 17 where the catalyst is separated therefrom. Then, the product material from which the catalyst has been separated is loaded by the pump 11 into the treated liquid storage tank 18. In the treated liquid storage tank 18, the product material is separated into a target product and a by-product. In this manner, a final product is obtained. Such treatment is repeatedly performed, and, thus, a target product is sequentially produced. Furthermore, if the reactor 13 can be opened and closed above the unfilled space, for example, when checking the state inside the reactor 13 or performing maintenance of the internal portion of the reactor 13, it is possible to access the inside of the reactor 13 by opening the top of the reactor 13.

Note that the treatment that separates the catalyst in the catalyst separating portion 17 and the treatment that separates the product material into a product and a by-product in the treated liquid storage tank 18 may be performed sequentially each time the product material is loaded, or may be performed at a time when the amount of product material loaded accumulates and reaches a certain amount. That is to say, the treatment in the reactor 13 is of a flow-type (flow through-type), but the treatment in the catalyst separating portion 17 and the treated liquid storage tank 18 on the path thereafter may be of a flow-type, or may be of a batch-type. Note that the flow-type may be referred to as a continuous-type.

Furthermore, there is no limitation on the chemical reaction caused to occur in the chemical reaction apparatus 1 according to this example, as long as it is a chemical reaction that is caused to occur by microwave irradiation itself or by heat due to microwave irradiation. For example, the chemical reaction may be production of biodiesel fuel through esterification or transesterification, may be production of ink raw material that is ester, or may be other chemical reactions. Furthermore, ultrasonic wave irradiation may or may not be performed together with microwave irradiation.

Simulation Results

Next, simulation results will be described. The simulations were performed using high-frequency three-dimensional electromagnetic field analyzer software "ANSYS (registered trademark) HFSS". In the simulation results, a portion with a light color (portion with a color close to white) is a portion having a high microwave intensity, and a portion with a dark color (portion with a color close to black) is a portion having a low microwave intensity.

Simulation 1

Figure 5A:
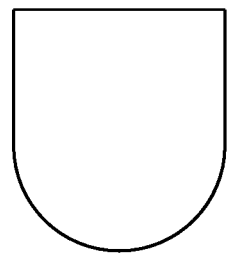
FIG. 5A is a diagram showing a cross-sectional shape of the reactor in simulations in this example.
Figure 6A:
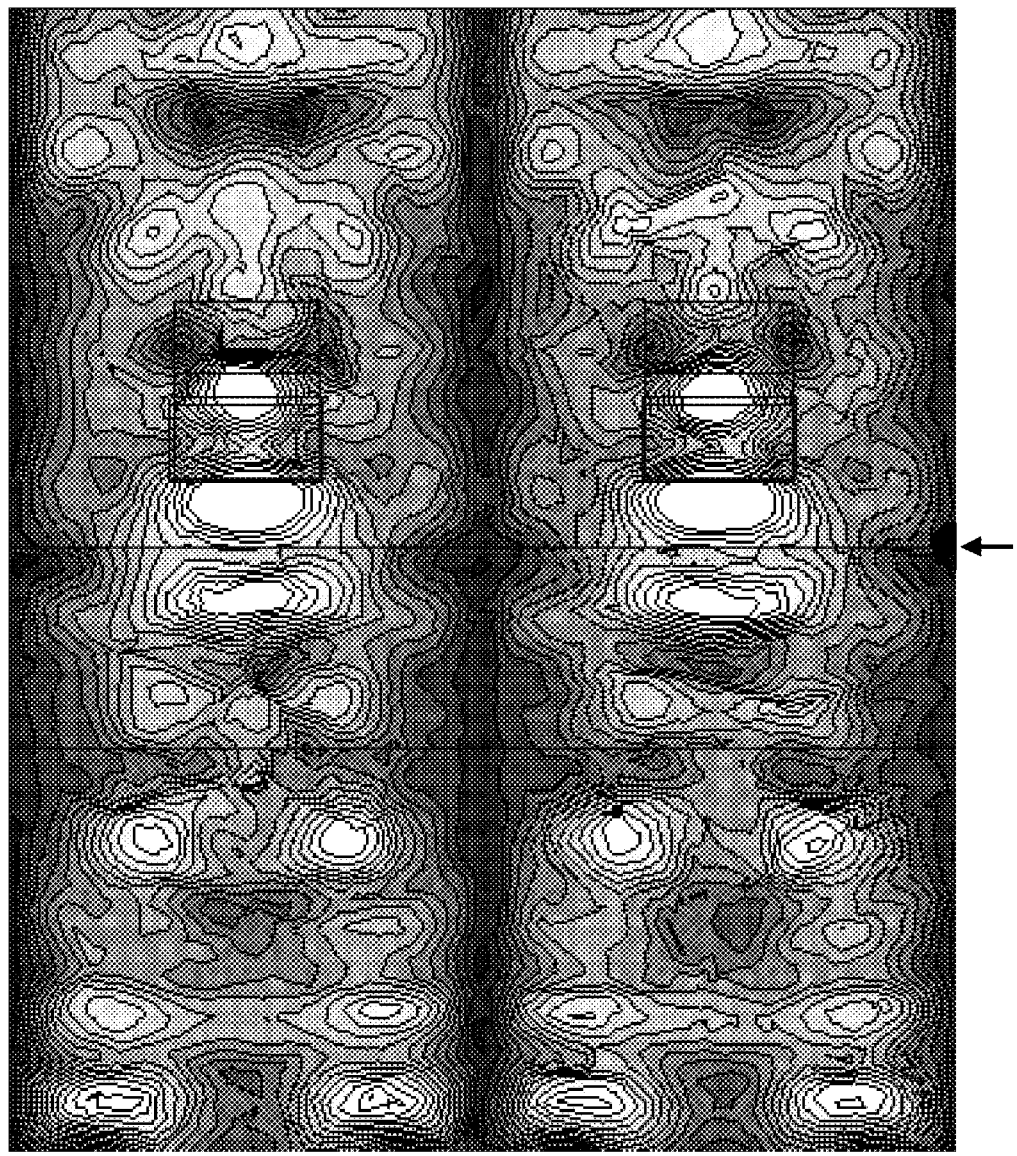
FIG. 6A is a diagram showing a simulation result ($\theta=15°$) in this example.
Figure 6B:
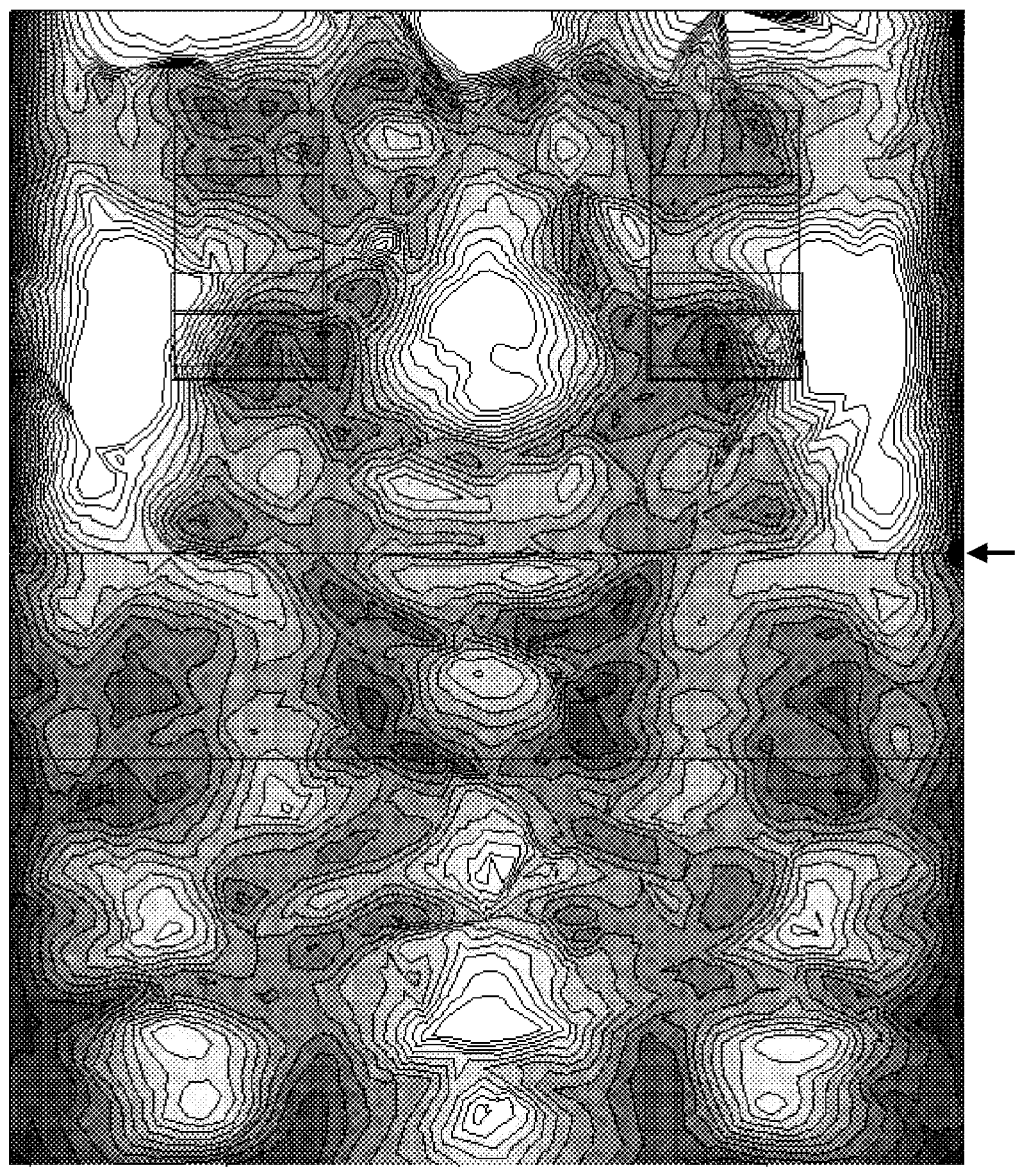
FIG. 6B is a diagram showing a simulation result ($\theta=30°$) in this example.
Figure 6C:
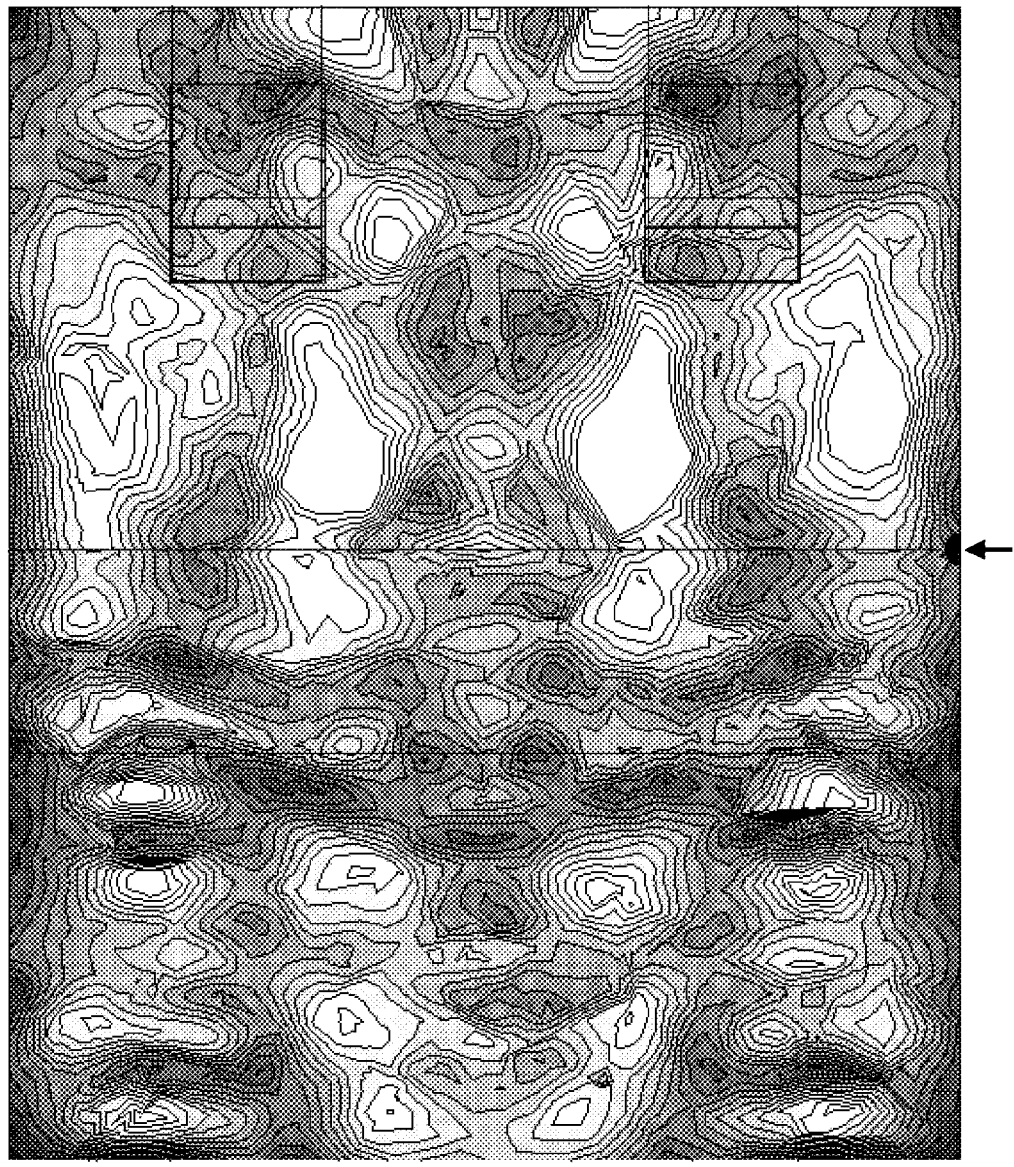
FIG. 6C is a diagram showing a simulation result ($\theta=45°$) in this example.
Figure 6D:
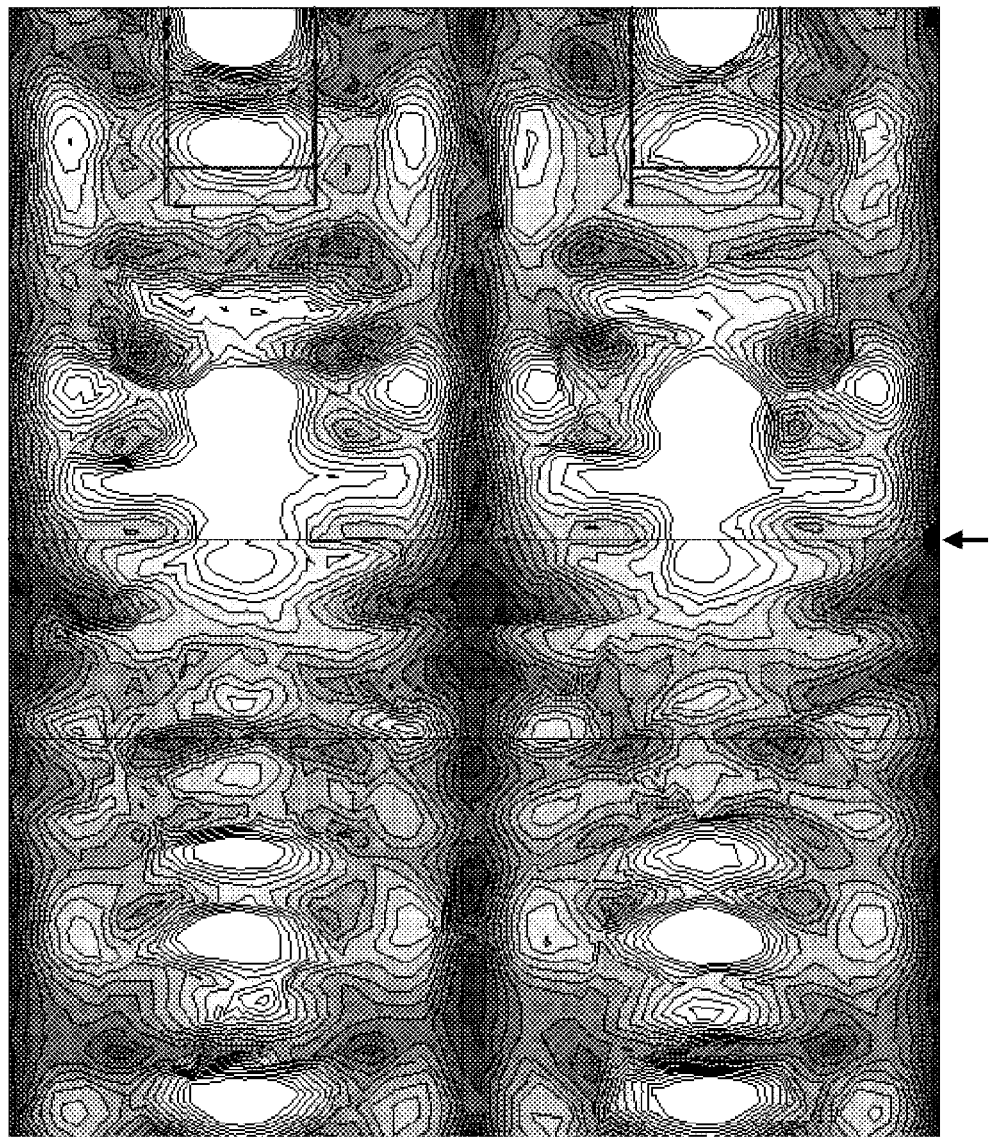
FIG. 6D is a diagram showing a simulation result ($\theta=60°$) in this example.
Figure 6E:
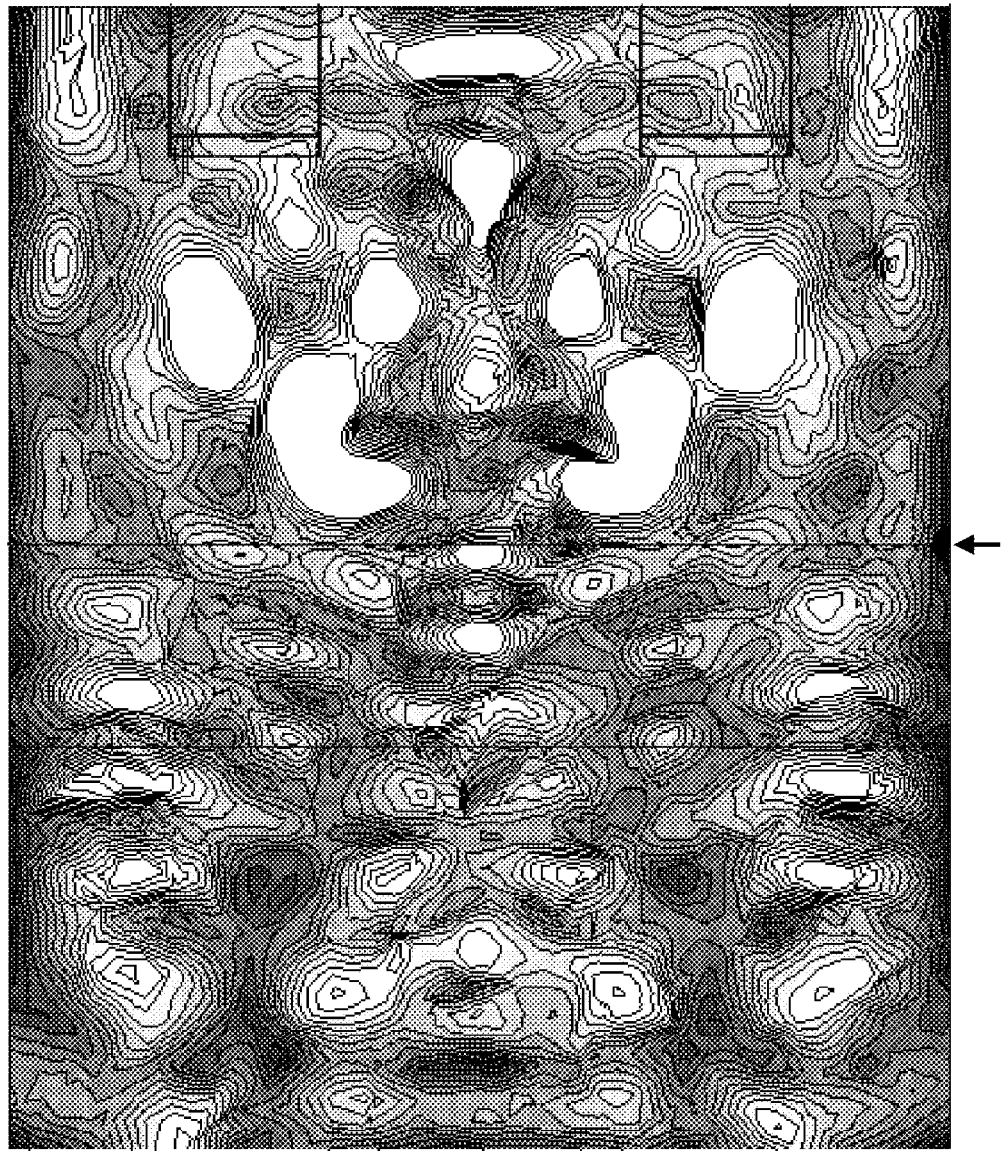
FIG. 6E is a diagram showing a simulation result ($\theta=75°$) in this example.
Figure 6F:
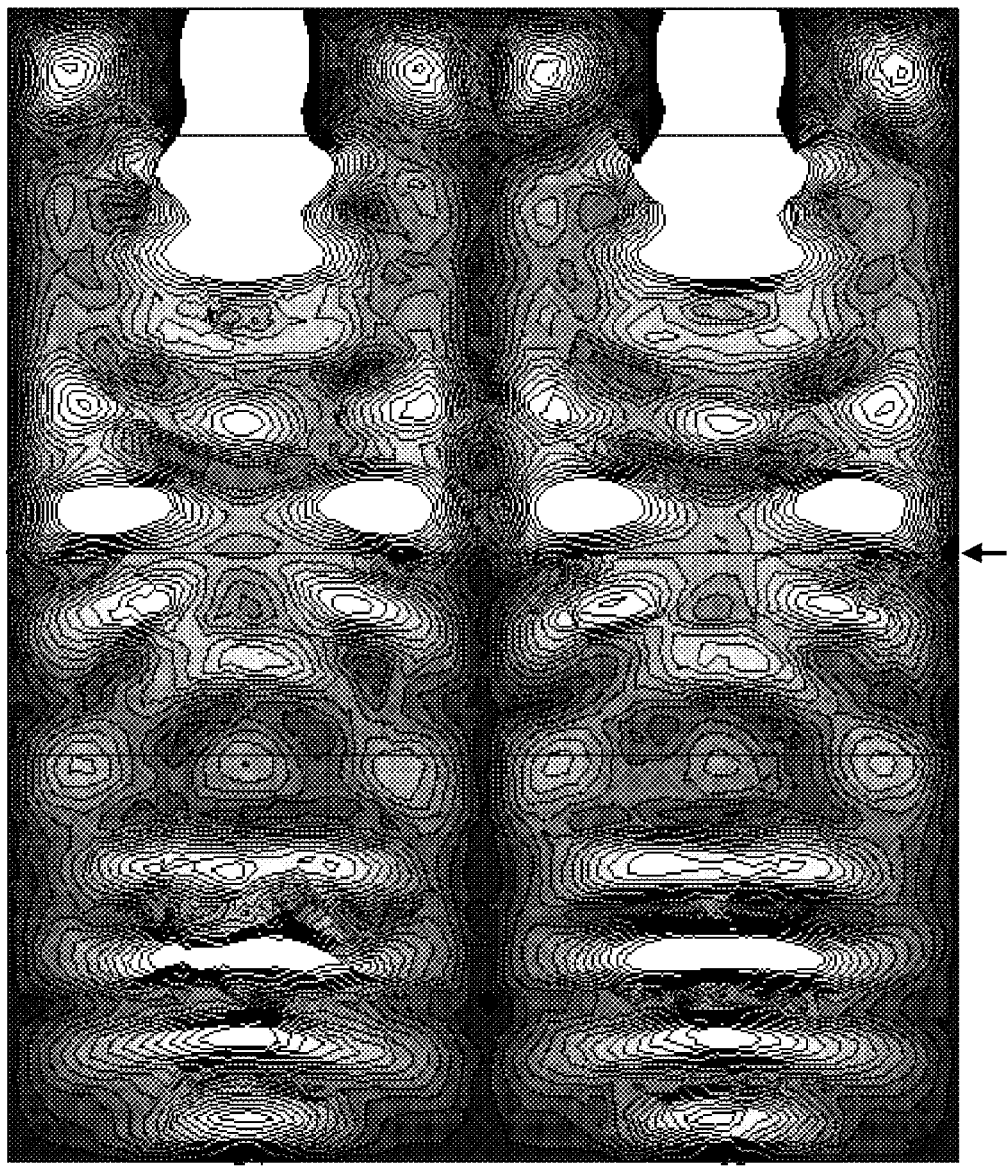
FIG. 6F is a diagram showing a simulation result ($\theta=90°$) in this example.

In this simulation, the angle $\theta$ formed by microwaves incident on the unfilled space and a liquid surface of a content was changed from 15° to 90°. FIGS. 6A to 6F show simulation results respectively corresponding to $\theta=15°$, 30°, 45°, 60°, 75°, and 90°. In each simulation result, the top of the reactor is flat both in the longitudinal direction and in the direction orthogonal to the longitudinal direction. That is to say, the reactor has a cross-sectional shape as shown in FIG. 5A. In FIGS. 6A to 6F, the liquid surface position of the content is indicated by an arrow. In FIGS. 6A to 6F, the longitudinal direction of the reactor matches the left-right direction in the drawings. That is to say, in FIGS. 6A to 6F, the reactor is viewed in the same direction as in FIGS. 1 and 2. In the case of $\theta=15°$ shown in FIG. 6A, most microwaves are reflected by the liquid surface and do not penetrate into the liquid. In FIG. 6A, a region having a low microwave intensity extends in the upper-lower direction around the middle, indicating that this portion is not properly irradiated with microwaves. In the case of $\theta=90°$ shown in FIG. 6F, microwaves penetrate into the liquid, but the microwaves in the liquid are so uneven that there are portions on which microwaves are concentrated and portions on which microwaves are not concentrated. Also in FIG. 6F, a region having a low microwave intensity extends in the upper-lower direction around the middle as in FIG. 6A. FIGS. 6B to 6E respectively correspond to $\theta=30°$, 45°, 60°, and 75°, and show that the microwave intensity distributions in the liquid are relatively uniform. Accordingly, it is seen that the microwave irradiation angle $\theta$ is preferably 30 to 75°. Especially in the case of $\theta=45°$ shown in FIG. 6C, the microwave intensity distribution in the liquid is uniform, and there is no microwave concentration in the upper portion in the reactor. Accordingly, it is seen that the microwave irradiation angle $\theta$ is more preferably around 45°. Thus, in Simulations 2 and 3 below, $\theta$ was set to 45°. Note that the microwave irradiation direction may be considered to be the longitudinal direction of a waveguide that transmits microwaves.

Simulation 2

Figure 7B:
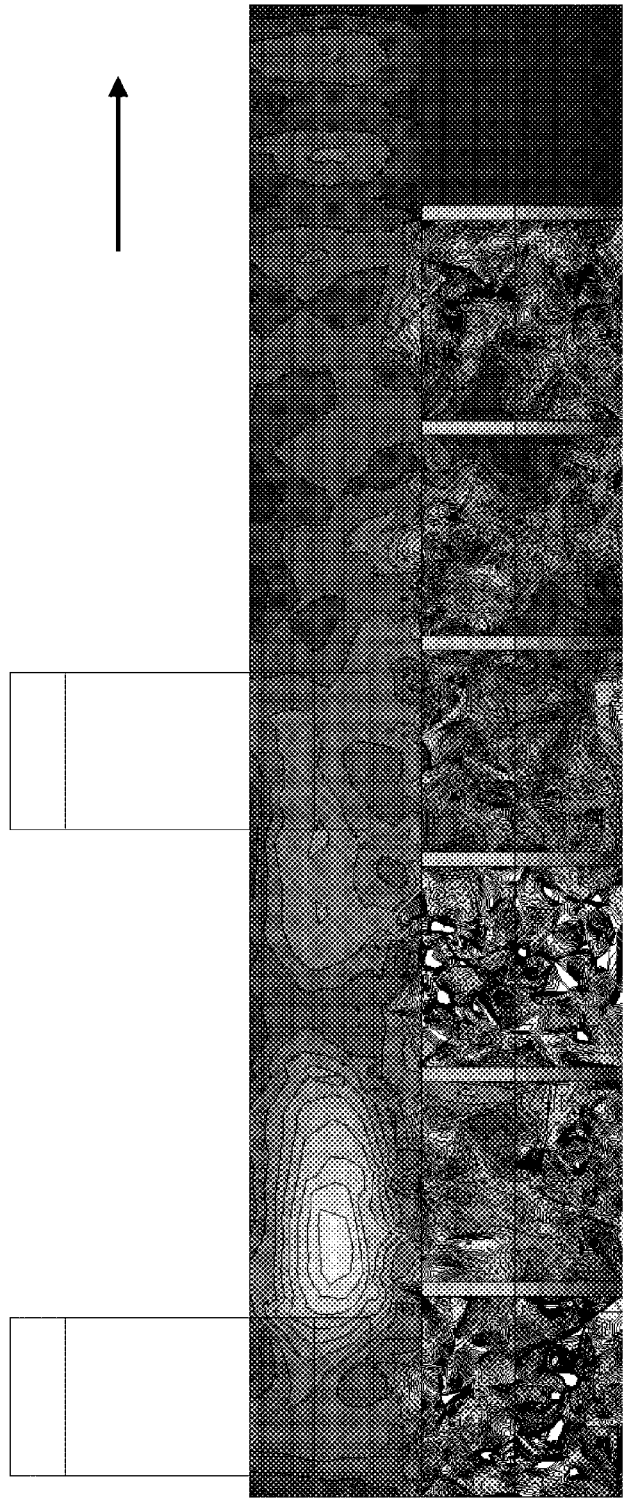
FIG. 7B is a diagram showing a simulation result (flat shape) in this example.

In this simulation, a case in which the top of the reactor 13 is curved with respect to the longitudinal direction of the reactor and a case in which the top does not have such a shape were compared. FIG. 7A shows a simulation result in the case where the top of the reactor 13 is curved with respect to the longitudinal direction, whereas FIG. 7B shows a simulation result in the case where the top does not have such a shape, that is, the case where the top of the reactor is flat instead of being curved with respect to the longitudinal direction. It was assumed that, in both cases, the top of the reactor is flat with respect to the direction orthogonal to the longitudinal direction. That is to say, the reactor has a cross-sectional shape as shown in FIG. 5A. In FIGS. 7A and 7B, the flow direction of the content is indicated by an arrow in the drawings. That is to say, in FIGS. 7A and 7B, the reactor is viewed in the same direction as in FIGS. 1 and 2. In both FIGS. 7A and 7B, the inside of the reactor is partitioned into seven chambers by partition plates that do not transmit microwaves. It was assumed that, in both cases, waveguides are connected to positions above the first chamber from the left and the fourth chamber from the left. In FIG. 7A, the chambers below the positions to which the waveguides 15 are connected have the largest microwave intensity, but the other chambers are uniformly irradiated with microwaves. On the other hand, in FIG. 7B, regardless of the chambers below the positions to which the waveguides are connected, the first chamber from the left and the third chamber from the left have a high microwave intensity, and microwaves do not enter the first chamber from the right at all. In this manner, if the top of the reactor is curved with respect to the longitudinal direction, the chambers are more uniformly irradiated with microwaves, and microwaves are not relatively concentrated. On the other hand, if the top of the reactor is flat with respect to the longitudinal direction, microwaves are concentrated, and uniform irradiation cannot be performed. Accordingly, it is seen that forming the top of the reactor 13 so as to be curved with respect to the longitudinal direction is effective for suppressing microwave concentration, thereby realizing more uniform microwave irradiation.

Simulation 3

Figure 8A:
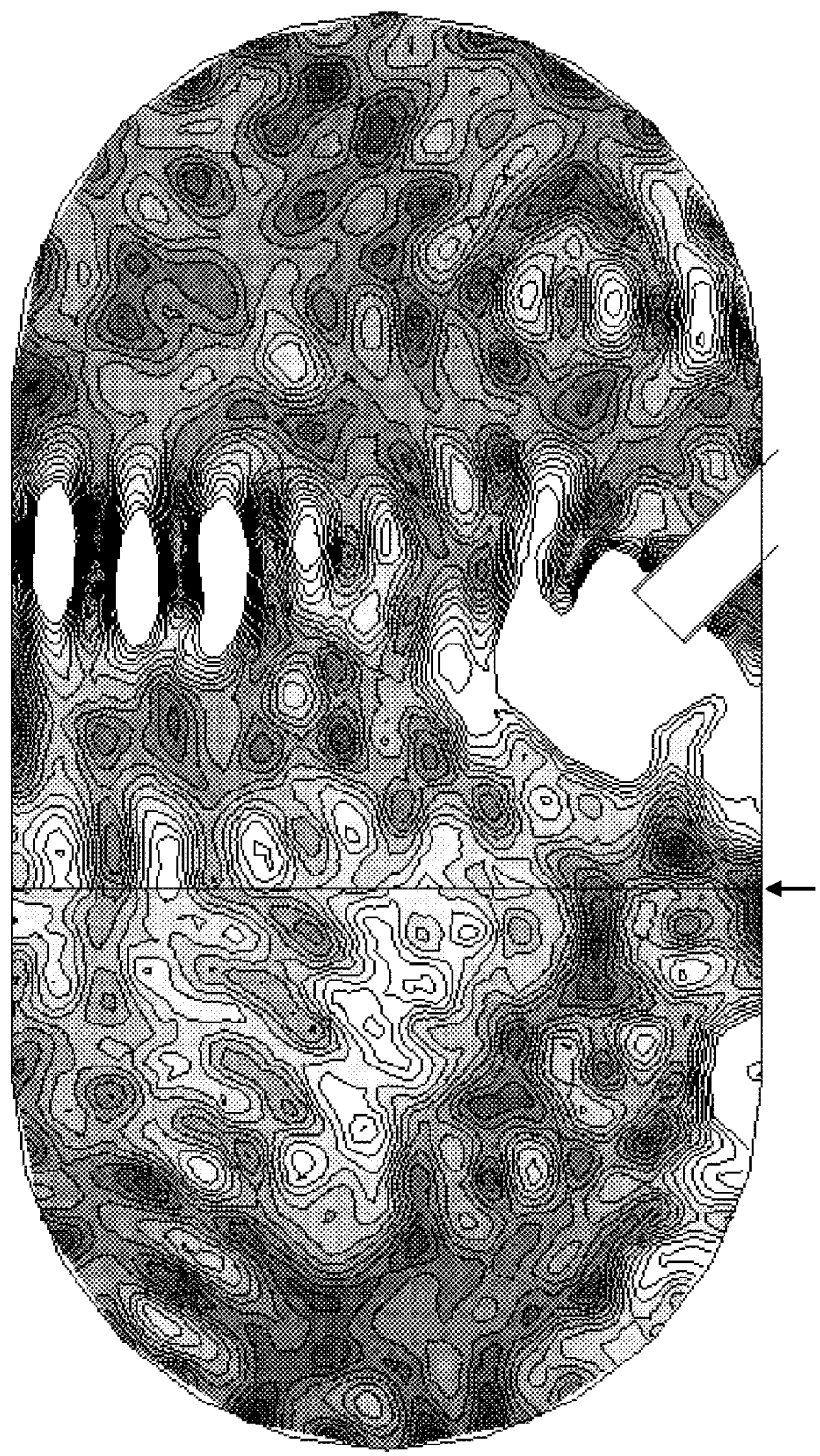
FIG. 8A is a diagram showing a simulation result (arched shape) in this example.
Figure 8B:
FIG. 8B is a diagram showing a simulation result (flat shape) in this example.

In this simulation, a case in which the top of the reactor 13 is arched with respect to the direction orthogonal to the longitudinal direction and a case in which the top does not have such a shape were compared. FIG. 8A shows a simulation result in the case where the top of the reactor 13 is arched with respect to the direction orthogonal to the longitudinal direction, whereas FIG. 8B shows a simulation result in the case where the top does not have such a shape, that is, the top of the reactor is flat with respect to the direction orthogonal to the longitudinal direction. It was assumed that, in both cases, the top of the reactor is flat with respect to the longitudinal direction. That is to say, the reactor has the same cross-sectional shape at any position in the longitudinal direction. In both FIGS. 8A and 8B, the liquid surface position of the content is indicated by an arrow. In FIGS. 8A and 8B, the reactor is viewed in the same direction as in FIG. 3. Note that the partition plates are not shown in FIGS. 8A and 8B. As shown in FIG. 8A, if the top of the reactor 13 is arched with respect to the direction orthogonal to the longitudinal direction, there is almost no microwave concentration seen in the upper portion in the reactor 13. On the other hand, as shown in FIG. 8B, if the top of the reactor is not arched with respect to the direction orthogonal to the longitudinal direction, there are portions on which microwaves are concentrated in the upper portion in the reactor. Especially in the upper right portion in FIG. 8B, microwaves are concentrated near the upper face of the reactor, and the upper face plate of the reactor may be abnormally heated. Accordingly, it is seen that forming the top of the reactor 13 so as to be arched with respect to the direction orthogonal to the longitudinal direction is effective for suppressing microwave concentration in the unfilled space.

It is also seen from the results of Simulation 3 that, if there is a portion in which the inner wall of the reactor 13 is bent at an angle of 90° or less (acute angle) (e.g., the upper right in FIG. 8B, etc.), microwaves may be concentrated on that portion. Accordingly, it is seen that the inner wall of the reactor 13 is preferably continuously formed at an angle more than 90° (obtuse angle) throughout the portion inside the reactor 13 or at least in the unfilled space in the reactor 13.

As described above, according to the chemical reaction apparatus 1 according to this example, if the top of the reactor 13 is curved with respect to the longitudinal direction of the reactor 13 or is arched with respect to the direction orthogonal to the longitudinal direction, microwave concentration on portions other than the content (e.g., on the unfilled space, etc.) can be suppressed, and the content can be more uniformly irradiated with microwaves. As a result, the content is properly heated, and a chemical reaction of the content is facilitated. In the case of a single mode, stationary microwaves are used, and, thus, it is easy to know portions on which electrical fields or magnetic fields are concentrated, whereas, in the case of a multi-mode, it is very difficult to know portions on which electrical fields or magnetic fields are concentrated. However, if the reactor has a shape as in the reactor 13 of the chemical reaction apparatus 1 according to this example, microwave concentration in the unfilled space and the like can be suppressed even in the case of the multi-mode. It seems that, since microwave concentration on portions other than a target portion can be suppressed, the energy efficiency can be improved.

Furthermore, if the angle θ formed by the microwaves incident on the unfilled space and the liquid surface of the content is 30° to 75°, the content can be more uniformly irradiated with the microwaves. Furthermore, if the angle θ is 45°, uniform irradiation can be more reliably realized, and microwave concentration in the unfilled space can be suppressed.

Furthermore, it seems that, if the microwaves are irradiated on a middle position of the liquid surface in the direction orthogonal to the longitudinal direction of the reactor 13, when the microwaves that were reflected by the liquid surface of the content are reflected by the top of the reactor 13, the possibility that the content is irradiated with the reflected microwaves is increased.

In the description above, the case has been mainly described where a content flowing inside the reactor 13 is irradiated with microwaves, but there is no limitation to this. For example, the configuration is also possible in which, after the reactor 13 is filled with a content and the loading of the content is stopped, the content is irradiated with microwaves via the unfilled space, and, after the microwave irradiation is ended, a new content is loaded into the reactor 13 so that the reacted content is discharged from the reactor. In this configuration, the content may be caused to flow and be irradiated with microwaves alternately in a repeated manner. Also in this case, that reactor 13 may be referred to as a horizontal flow-type reactor because the content horizontally flows therein. In this case, also when the new content is being loaded into the reactor 13, the content may be irradiated with microwaves. As described above, the reactor 13 may be used as a batch-type reactor. If the reactor 13 is used as a batch-type reactor, for example, an outlet for discharging a content may be provided at the bottom of the reactor 13.

In this example, the case has been described where the mixing portion 12 that mixes the raw material and the catalyst is provided, but there is no limitation to this. For example, if a premixure of the raw material and the catalyst is used, if the mixing is also performed by the reactor 13, if the solid catalyst that flows inside the reactor 13 is retained in the reactor 13, if a solid catalyst forming a fixed bed is used instead of the solid catalyst that flows inside the reactor 13, or if no catalyst is used, the chemical reaction apparatus 1 does not have to be provided with the mixing portion 12. Note that, if a solid catalyst forming a fixed bed is used, typically, the solid catalyst forming a fixed bed is provided inside the reactor 13. The solid catalyst forming a fixed bed may be fixed, for example, by being pasted on the inner wall of the reactor 13, or by being placed in a catalyst filled layer, a column, or the like inside the reactor 13. Examples of the shape of the solid catalyst include various grains, a cylinder (that may or may not be hollow, for example), a sphere, a pellet, a ring, a shell, a honeycomb, a foam, a fiber, a cloth, a plate, and other shapes.

Furthermore, in this example, the case has been described where the reactor 13 has four chambers 31 to 34 that are continuously arranged in series as shown in FIG. 2, but the number of chambers may be one, or may be two or more. Typically, as the number of chambers increases, a situation can be more effectively prevented in which the raw material flows in a shortcut from the inlet to the outlet of the reactor 13.

Furthermore, in this example, the case has been described where the chemical reaction apparatus 1 is provided with the temperature measuring portions 25 and the microwave control portion 16, but there is no limitation to this. For example, if it is possible to keep the temperature inside the reactor 13 at a desired temperature or in a desired temperature range by setting the output of microwaves to a predetermined value, the control of the output of microwaves using the temperature does not have to be performed.

Furthermore, in this example, the case has been described where the catalyst separating portion 17 is provided on the path after the reactor 13, but there is no limitation to this. If the catalyst does not have to be separated by the chemical reaction apparatus 1 according to this example, as in the case in which the catalyst is separated by another apparatus, the case in which the solid catalyst that flows inside the reactor 13 is retained in the reactor 13, the case in which a solid catalyst forming a fixed bed is used instead of the solid catalyst that flows inside the reactor 13, or the case in which no catalyst is used in the chemical reaction in the reactor 13, the catalyst separating portion 17 does not have to be provided.

Furthermore, in this example, the case has been described where the raw material and the catalyst are mixed and loaded into the reactor 13, but there is no limitation to this. For example, only the raw material may be loaded into the reactor 13. Furthermore, if the raw material and the catalyst are not mixed, only the raw material may flow inside the reactor 13. That is to say, the content of the reactor 13 may be, for example, a mixture of multiple raw materials. Furthermore, even in the case where the raw material and the catalyst are not mixed, for example, the raw material and the catalyst may flow inside the reactor 13 when the solid catalyst that flows inside the reactor 13 is retained in the reactor 13. Furthermore, if the raw material and the catalyst are not mixed, the mixing portion 12 may, for example, mix the raw material, or mix the raw material (substrate) and the reactant. Furthermore, if the raw material and the like do not have to be mixed, the chemical reaction apparatus 1 does not have to be provided with the mixing portion 12 as described above.

Furthermore, in this example, the case has been described where one or more agitation units 23 that agitate the raw material inside the reactor 13 are provided, but there is no limitation to this. For example, if the reactor 13 is configured such that the entire raw material can be easily irradiated with microwaves (e.g., if the inner diameter of the reactor 13 is small, etc.), the agitation units 23 do not have to be provided.

Furthermore, in this example, the case has been described where the chemical reaction apparatus 1 is provided with the treated liquid storage tank 18, but there is no limitation to this. For example, a mixture of the product material and the by-product discharged from the chemical reaction apparatus 1 may be subjected to extraction of the product material and the like in another apparatus.

Figure 5B:
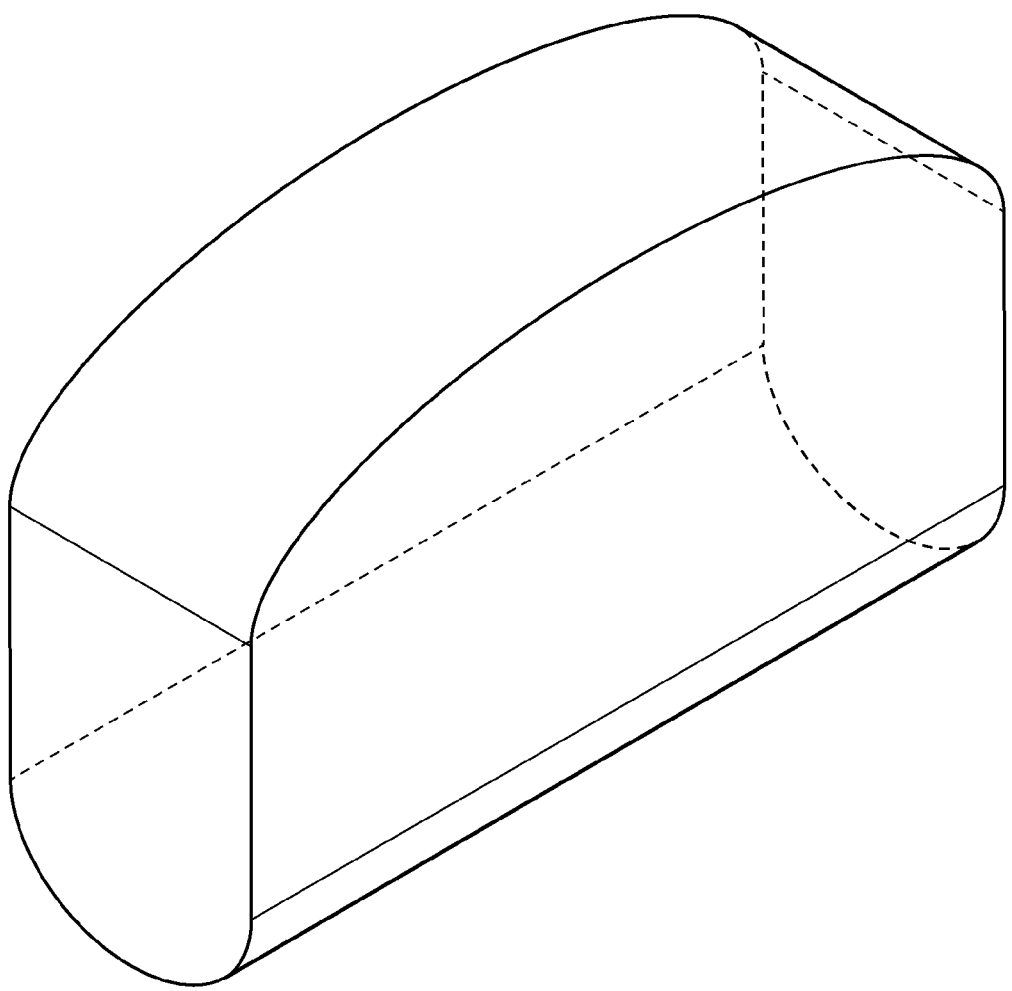
FIG. 5B is a side-top profile view of the reactor in this example.

Furthermore, in this example, the case has been described where the top of the reactor 13 is curved with respect to the longitudinal direction of the reactor 13, but there is no limitation to this. Also, the case has been described where the top of the reactor 13 is arched with respect to the direction orthogonal to the longitudinal direction of the reactor 13, but there is no limitation to this. For example, configurations are also possible in which the top of the reactor 13 is curved with respect to the longitudinal direction of the reactor 13 and is not arched with respect to the direction orthogonal to the longitudinal direction of the reactor 13 (see FIG. 5B), is not curved with respect to the longitudinal direction of the reactor 13 and is arched with respect to the direction orthogonal to the longitudinal direction of the reactor 13, or is not curved with respect to the longitudinal direction of the reactor 13 and is not arched with respect to the direction orthogonal to the longitudinal direction of the reactor 13.

Furthermore, in this example, the case has been described where the angle formed by microwaves incident on the unfilled space and a liquid surface of the content is 30 or more and 75 degrees or less, but there is no limitation to this. The angle may be out of this range.

Furthermore, in this example, the case has been described where microwaves are irradiated on a middle position in the direction orthogonal to the longitudinal direction of the reactor 13, but there is no limitation to this. The microwaves may be irradiated on other positions.

Furthermore, it will be appreciated that the present invention is not limited to the example set forth herein, and various modifications are possible within the scope of the present invention.

As described above, the chemical reaction apparatus according to the present invention is effective in that a situation where microwaves are concentrated on a partial portion in a reactor can be suppressed and a content can be more uniformly irradiated with the microwaves, and, thus, this apparatus is useful, for example, as a chemical reaction apparatus that heats a content with microwaves.

The invention claimed is:

1. A chemical reaction apparatus, comprising:
   a horizontal flow reactor in which a liquid content horizontally flows with an unfilled space being provided thereabove;
   a plurality of partition plates disposed within the reactor, partitioning the reactor into multiple chambers arranged in series;
   a plurality of microwave generators generating microwaves;
   a plurality of waveguides transmitting the microwaves generated by the plurality of microwave generators to the unfilled space in the reactor;
   wherein a top of the reactor is curved projecting upward above the plurality of chambers and with respect to a flow direction of the content,
   wherein the top of the reactor is flat with respect to a direction orthogonal to the flow direction, and
   wherein the reactor comprises a shape horizontally extending in the flow direction.

2. The chemical reaction apparatus according to claim 1, wherein an angle formed by microwaves incident on the unfilled space and a liquid surface of the content is 30 to 75 degrees.

3. The chemical reaction apparatus according to claim 2, wherein the angle formed by the microwaves incident on the unfilled space and the liquid surface of the content is 45 degrees.

4. The chemical reaction apparatus according to claim 1, wherein the plurality of partition plates do not transmit microwaves.

5. The chemical reaction apparatus according to claim 1, wherein the top of the reactor is a single arch above the plurality of chambers.

6. The chemical reaction apparatus according to claim 1, wherein more waveguides in the plurality of waveguides are connected to the reactor at an upstream side than at a downstream side.

7. The chemical reaction apparatus according to claim 1, wherein the unfilled space is continuous across the plurality of chambers inside the reactor.

* * * * *